United States Patent [19]
West et al.

[11] Patent Number: 5,756,511
[45] Date of Patent: May 26, 1998

[54] METHOD FOR TREATING SYMPTOMS OF A NEURODEGENERATIVE CONDITION

[75] Inventors: James W. West, Seattle; David W. Leung, Mercer Island; J. Peter Klein, Vashon; Gail E. Underiner, Brier; Anil M. Kumar, Seattle, all of Wash.

[73] Assignee: Cell Therapeutics, Inc., Seattle, Wash.

[21] Appl. No.: 416,270

[22] Filed: Apr. 3, 1995

[51] Int. Cl.$^6$ .................................................. A01N 43/90
[52] U.S. Cl. .................................................. 514/263
[58] Field of Search .................................. 514/263

[56] References Cited

PUBLICATIONS

Yankner et al., *The New England Journal of Medicine*, vol. 325, No. 26, 1991, pp. 1849–1857, "β-Amyloid and the Pathogenesis of Alzheimer's Disease".
Behl et al., *Cell*, vol. 77, 1994, pp. 817–827, "Hydrogen Peroxide Mediates Amyloid βProtein Toxicity".
Ashall et al., *TEBS*, vol. 19, 1994, pp. 42–46, "Role of the β-amyloid Precursor Protein in Alzheimer's Disease".
Hardy et al., *Science*, vol. 256, 1992, pp. 184–185, "Alzheimer's Disease: The Amyloid Cascade Hypothesis".
Kosik, *Science*, vol. 256, 1992, pp. 780–783, "Alzheimer's Disease: A Cell Biological Perspective".
Attardi et al., *Cold Spring Harbor Symposia on Quantitative Biology*, vol. L1, 1986, pp. 103–114, Seven Unidentified Reading Frames of Human Mitochondrial DNA Encode Subunits of the Respiratory Chain NADH Dehydrogenase.
Flier, Jeffrey; "β-Amyloid and the Pathogenesis of Alzheimer's Disease" Sem. Med. vol. 325 No. 26 p. 1849.
Behl, C. "Hydrogen Peroxide Mediates Amyloid β Protein Toxicity" Cell. vol. 77 pp. 817–827, Jun. 17, 1994.
Ashall, Frank et al; "Role of the β–Amyloid Precursor Protein in Alzheimer's Disease. " TIBS 19, Jan. 1994 pp. 42–47.
Hardy, John et al; Alzheimer's Disease: The Amyloid Cascade Hypothesis; (Perspective) Science, vol. 256 pp. 184–185 (1992).

Kosik, Kenneth S. "Alzheimer's Disease: A Cell Biological Perspective" Science, vol. 256 (1992) pp. 780–783.
Attardi G, "Seven Unidentified Reading Frames of Human Mitochondrial DNA Encode Subunits of the Respiratory Chain NADH Dehydrogenase." vol. LI, (1986) pp. 103–114.

*Primary Examiner*—James J. Seidleck
*Assistant Examiner*—Terressa Mosley
*Attorney, Agent, or Firm*—Stephen Faciszewski

[57] ABSTRACT

A method for treating symptoms of Alzheimer's Disease by administering an effective amount of a compound, racemate, isolated R or S enantionmer, solvate, hydrate or salt having the formula:

X—terminal heterocyclic moiety.

In the above formula, the terminal heterocyclic moiety is a 3,7-dimethylxanthinyl, 3-methylxanthinyyl or xanthinyl moiety and X is:

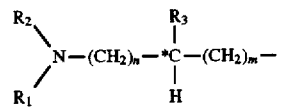

n is zero or an integer from one to four; and m is an integer from seven to fourteen. For compounds useful in the inventive method, $R_1$ and $R_2$ are hydrogen, a straight or branched chain alkyl, alkenyl or alkynyl of up to twenty carbon atoms in length or —$(CH_2)_w$—$R_5$. w may be an integer from one to twenty and $R_5$ is preferably an hydroxyl, halo $C_{1-8}$ alkoxyl group or a substituted or unsubstituted carbocycle or heterocycle. $R_3$ in compounds useful in the inventive method may be either an hydroxyl group, an oxygen atom, the single bond represented being instead a double bond, or —O—$R_4$, $R_4$ being a $C_{1-6}$ oxoalkyl.

5 Claims, 3 Drawing Sheets

METHOD FOR TREATING SYMPTOMS OF A NEURODEGENERATIVE CONDITION

TECHNICAL FIELD OF THE INVENTION

The invention provides a method for treating symptoms of neurodegenerative diseases by administering agents that are effective for inhibiting amyloid precursor protein (APP) expression.

BACKGROUND OF THE INVENTION

Neurodegenerative diseases, long known to cause, inter alia, dementia, have presented unique problems for investigators in developing therapies. Recently, researchers have acquired new insight into disease mechanisms of neurodegenerative conditions, as contemporary analytical methods have provided meaningful information about their neuropathology.

In aging, many elderly people suffer from Alzheimer's Disease ("AD"). In fact, AD affects one in thirty people over 65 and one in five people over 80, with more individuals being affected as the general population ages. Symptoms of neurodegeneration vary; but generally, AD symptoms correlate to some degree of both recent and more severe, long-term memory deficit. Other symptoms associated with neurodegeneration include loss of language skill, ability to think abstractly, judgment and spatial orientation, usually visual. In more advanced stages of memory deficit, attention and cognitive skills deteriorate. Victims will often become paranoid and are prone to having delusions. Generally, affected individuals experience confusion and develop motor skill deficiency. Dementia increases as the disease progresses, brought about by neuronal death and atrophy of cerebral tissue. Neuronal death is primarily limited to specific areas in the brain and mainly affects cholinergic neurons.

AD is a heterogeneous disease that can be divided into two general categories, Familial AD ("FAD") and sporadic AD ("SAD"). FAD may be subdivided further into early and late onset, based on an individual's age at onset, and is characterized by strong genetic components involving mutations at genetic loci on chromosomes 21, 19 and 14. These genetic loci account for most diagnosed cases of FAD. SAD has no identified genetic component and little is known about its cause. SAD may develop as the result of a disregulated inflammatory state in the central nervous ("CNS") caused by the cumulative effects of traumas and viral or bacterial infections experienced during an otherwise normal life span.

Although historically, knowledge of disease pathology in AD was limited, in recent years researchers have obtained a much greater understanding of AD pathology. For example, the presence of abnormal intracellular cytoskeletal filaments associated with neurofibrillary tangles may correlate to the onset of dementia. Flier et al. (1991).

Even more recently, extra cellular deposits of senile plaques were identified as characteristic of cerebral tissues in Alzheimer's victims. These senile plaques contain accumulated β-amyloid peptide ("βAP"). βAP is a fragment peptide of the larger amyloid precursor protein ("APP"), which appears in both normal healthy cells and the cells of individuals with AD. APP is a membrane glycoprotein.

Structurally, approximately two-thirds of βAP is extra cellular, the remaining third of βAP being integrated into the membrane. Functionally, shorter peptides contained within βAP can spontaneously form amyloid-like fibrils in a β-sheet conformation. Kosik et al. (1992). These amyloid fragments undermine neuron viability.

Hardy et al (1992) believe that βAP is the causative agent of AD pathology. They present that the neurofibrillary tangles, cell loss, vascular damage and dementia follow as a direct result of this deposition. Research has identified how APP proteolysis leads to βAP deposition. APP processing might occur via one of two pathways: 1) cleavage within βAP by secretase, generating peptide products that do not contain complete βAP, and thus, cannot precipitate to form amyloid; and 2) cleavage in the endosomal-lysosomal compartment, generating intact βAP that precipitates to form amyloid. The latter process has been implicated in the AD mechanism.

In support of this hypothesis, Ashall et al. (1994) disclose that the two pathways discussed in Hardy et al. are but two of numerous proteolytic pathways which lead to secretion of various fragments of APP or intracellular fragmentation and degradation. Of three major protease cleavage sites, two cleavage sites, the β-secretase and γ-secretase sites, yield β-peptide. Normal cells produce an extra cellular, soluble form of βAP, detected in normal cerebrospinal fluid and blood. Ashall et al. did not characterize the α-, β- or γ-secretases.

As discussed above, one of the earliest events in AD development is the extra cellular deposition of βAP in cerebral tissue. βAP is a 43 amino acid peptide consisting of 28 residues from extra cellular domain and 11 to 14 residues of the transmembrane region of the APP parent.

APP, constituitively expressed in the brain and other tissues, is a multi-domain protein with a large extra cellular amino segment followed by a single membrane spanning region and a small intracellular carboxyl terminus. Alternative splicing of the primary transcript gives rise to mRNA coding for at least five isoforms of APP distinquished by amino acid length and the absence or presence of a protease inhibitor domain. The expression of specific isoforms can vary according to cell type, but the function of individual isoforms in normal tissue and in AD is still unclear. APP may normally function in cell-cell and cell-matrix adhesion, or more recently, as an anti-clotting factor based on its ability to inhibit clotting factor IXa.

As discussed by Hardy et al., APP is post-transcriptionally modified by O- and N-glycosylation, phosphorylation and sulfanation. Additionally, APP is processed through proteolytic pathways acting at three major sites. In the normal brain, APP is predominantly processed at the α-secretase site within the βpeptide, preventing formation of βAP and releasing a soluble form of APP truncated at the carboxy terminus. The β-secretase or γ-secretase can work independent of each other to release heterogenous forms of secreted APP, or working together, lead to formation of amylogenic βAP.

Trisomy 21, resulting in Down's Syndrome ("DS"), is the earliest recognized genetic route to AD-like pathologies. Individuals with DS develop microscopic signs of AD at 20–30 years of age, nearly 50 years earlier than other non-DS individuals with AD. The APP gene is located on human chromosome 21.

Overexpression of APP, due to gene dosage, leads to accelerated amyloid deposition in DS. Some forms of FAD have been linked to point mutations in the APP gene. Six families demonstrating early-onset FAD carried a valine to isoleucine mutation at position 717 with the transmembrane domain. A second mutation in the APP gene, glutamine for glutamic acid at position 693, was documented in all individuals with hereditary cerebral hemorrhage with amylodosis-Dutch type. Although this research supports an integral role for APP and a genetic component in the development of AD, only a fraction of FAD correlates with abnormalities of chromosome 21.

Two FAD groups have demonstrated a strong linkage between a large percentage of early onset FAD and a locus on the long arm of chromosome 14. Although FAD is a genotypically heterogeneous disease caused by inherited co-dominant mutations within at least three genes, consideration of the proteins encoded at the FAD loci indicate FAD may be less phenotypically heterogeneous. Irrespective of genetic mutation, APP is central to the biochemical abnormality seen for FAD.

Overexpression of APP, in trisomy 21, may saturate the normal proteolytic processing pathways of APP with excess APP processed to βAP. Increased βAP leads to the accelerated amyloid deposition and development of neuritic plaques. As a chromosome 14 locus has not yet been identified, no conclusion has yet been drawn concerning it; however, candidate loci include proteins involved in expression and processing of APP. The inventive method therefore targets reduction in APP expression which would subsequently reduce βAP accumulation and would therefore retard disease progression.

SAD can be defined as AD with no identified genetic component and unknown etiology. Researchers have proposed that environmental factors may contribute to deposition of βAP and amyloidosis in the CNS. Potentially, hereditary or environmental queues initiate an inflammatory response in the CNS, which if unchecked by normal regulatory pathways results in the pathological progression of AD. This hypothesis is supported by epidemiological evidence that patients on long term non-steroidal anti-inflammatory drug therapies have significantly lower incidence of AD (MeGeer et al., 1992).

Inflammatory cytokines IL-1, Il-6 and TNFα are produced and secreted in the CNS and surface receptors for these cytokines are found within neuronal populations affected by AD. IL-1and TNFα, known mediators of inflammatory response, are elevated in AD cerebral tissue and have been shown to stimulate expression of IL-6 and APP. Pathological stimulation or brain trauma causes significant increases in TNFα levels in the brain and subsequent deposition of βAP. Specifically, Woodroofe et al. (1991) and Griffin et al. (1989) reported elevated levels of Il-1and IL-6 following head injury and in cerebral spinal fluid of AD patients and DS individuals, respectively.

Il-6 stimulates the expression of the protease inhibitor α$_2$macroglobulin in human neuroblastoma cell, which in conjunction with α antichymotrypsin are found in neuritic plaques in the brains of AD patients and DS individuals. These protease inhibitors affect APP processing. Human astrocytoma cells produce IL-6 when stimulated with IL-1 or TNFα and PC12 cells produce increased levels of APP when stimulated with IL-6.

Despite the level of skill in the art, at present, existing therapies aim at enhancing cerebral acetycholine levels with acetyl cholinesterase inhibitors. Unfortunately, acetyl cholinesterase inhibitor therapy can have severe adverse side effects.

Thus, there is a need in the art to find therapeutic agents to treat neurodegenerative diseases. The present invention has further advanced our understanding of the disease process, resulting in therapeutic compounds and methods for treating AD.

SUMMARY OF THE INVENTION

In conducting research aimed at identifying specific agents capable of reducing or eliminating deleterious accumulation of βAP, the inventors have discovered this inventive method for treating disease symptoms of AD. The heretofore unknown method addresses the problem of βAP accumulation by administering agents that inhibit expression of a parent protein, APP. The inventive method thus permits treatment of neurodegenerative symptoms by specifically reducing βAP accumulation by inhibiting expression of APP, therefore reducing the amount of available parent protein, APP.

The inventive method therefore responds to an unmet need in treating symptoms of subjects with AD. The inventive method comprises inhibiting expression of APP. By inhibiting APP expression, accumulation of βAP is reduced.

Inhibiting APP expression is achieved by administering an effective amount of a pharmaceutically acceptable compound, racemate, isolated R or S enantionmer, solvate, hydrate or salt having the formula:

X —terminal heterocyclic moiety.

In the above formula, the terminal heterocyclic moiety is a 3,7-dimethylxanthinyl, 3-methylxanthinyl or xanthinyl moiety and X is:

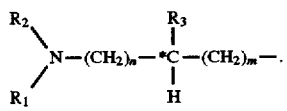

*C is a chiral carbon atom; n is zero or an integer from one to four; and m is an integer from seven to fourteen. For compounds useful in the inventive method, $R_1$ and $R_2$ are hydrogen, a straight or branched chain alkyl, alkenyl or alkynyl of up to twenty carbon atoms in length or —(CH$_2$)$_w$ R$_5$. w may be an integer from one to twenty and R$_5$ is preferably an hydroxyl, halo C$_{1-8}$ alkoxyl group or a substituted or unsubstituted carbocycle or heterocycle. R$_3$ in compounds useful in the inventive method may be either an hydroxyl group, an oxygen atom (the single bond represented being instead a double bond), or —O—R$_4$. R$_4$ being a C$_{1-6}$ oxoalkyl.

The inventive method is particularly adapted to permit treatment of various symptoms of AD. Preferably, the inventive method treats one or more of the following symptoms: recent memory deficit; severe memory deficit; attentive and cognitive skill deterioration; loss of language, abstract thinking, judgment and visual-spatial orientation skills; paranoia and delusion; motor deficiency; global confusion and dementia.

DETAILED OF PREFERRED EMBODIMENT

Figure 1:
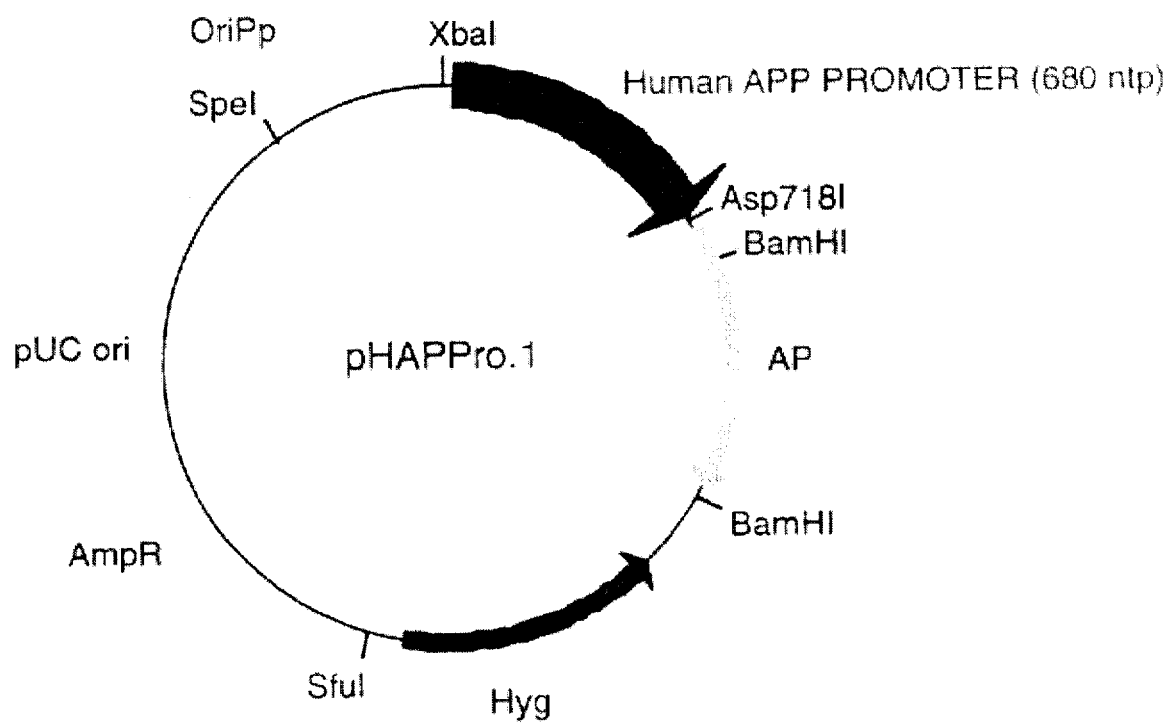
FIG. 1 is a promoter-alkaline phosphatase reporter gene construct for pHAPPro. 1.

The inventive method therefore provides a heretofore unknown solution for reducing accumulation of βAP and thereby treating symptoms of AD.

The inventive method permits treatment of one or more disease symptoms of AD including, but not limited to, recent memory deficit; severe memory deficit; attentive and cognitive skill deterioration; loss of language, abstract thinking, judgment and visual-spatial orientation skills; paranoia and delusion; motor deficiency; global confusion and dementia. The inventive method comprises inhibiting APP expression, thereby reducing accumulation of βAP, by administering a compound capable of inhibiting expression of APP.

Compounds

Many compounds, as exemplified below, show activity for inhibiting expression of APP. In the inventive method, the inhibitive compounds or a pharmaceutically acceptable salt, hydrate or solvate thereof, can be administered in a conventional dosage form as discussed below to a human suffering from any of the described symptoms.

The inventive method employs these small organic molecules as representative of compounds that exhibit activity for treating symptoms of AD by directly interfering with APP expression and thus reducing or eliminating accumulation of neurotoxic βAP, which correlates to tissue destruction in AD. These inhibitive compounds may be one or more of the compounds selected from the following compounds.

Compounds useful in the inventive method are a racemate, isolated R or S enantionmer, solvate, hydrate or salt having the formula:

X —terminal heterocyclic moiety, wherein the terminal heterocyclic moiety is a 3,7-dimethylxanthinyl, 3-methyl-7-pivoloylxanthinyl, 3-methylxanthinyl or xanthinyl moiety and X is:

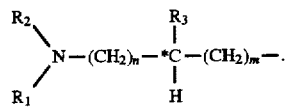

$R_1$ and $R_2$ are hydrogen, a straight or branched chain alkyl, alkenyl or alkynyl of up to twenty carbon atoms in length or —$(CH_2)_wR_5$. If $R_1$ or $R_2$ is —$(CH_2)_wR_5$, w may be an integer from one to twenty and $R_5$ may be an hydroxyl, halo, $C_{1-8}$ alkoxyl group or a substituted or unsubstituted carbocycle or heterocycle. Alternatively, $R_1$ and $R_2$ may jointly form a substituted or unsubstituted, saturated or unsaturated heterocycle having from four to eight carbon atoms, N being a hetero atom of the resulting heterocycle. $R_3$ may be either an hydroxyl group, an oxygen atom (wherein the single bond structurally represented is instead a double bond), or —O—$R_4$, $R_4$ being a $C_{1-6}$ oxoalkyl.

In these representative compounds, a total sum of carbon atoms comprising $R_1$ or $R_2$ and $(CH_2)n$ and $(CH_2)m$ preferably does not exceed forty.

In more preferred compounds useful in the inventive method, $R_5$ may be hydroxy, chloro, fluoro, bromo, or $C_{1-6}$ alkoxyl, or a substituted or unsubstituted, saturated or unsaturated heterocycle having from four to seven carbon atoms, more preferably, a mono-, di- or tri-substituted carbocycle or heterocycle. Preferred carbocycles or heterocycles have one or two-fused rings. Representative compounds of the above-described compound genus which are useful in the inventive method for treating symptoms of a neurodegenerative condition include, but are not limited to:

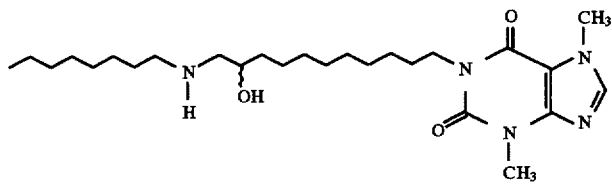

2576 1-(11-Octylamino-10-hydroxyundecyl)-3,7-dimethylxanthine

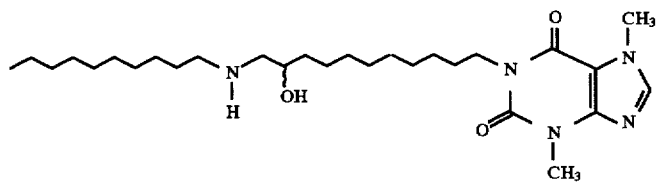

2583 1-(11-Decylamino-10-hydroxyundecyl)-3,7-dimethylxanthine

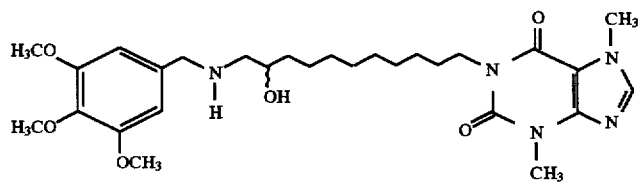

3501 1-[11-(3,4,5-Trimethoxybenzylamino)-10-hydroxyundecyl]-3,7-dimethylxanthine -continued

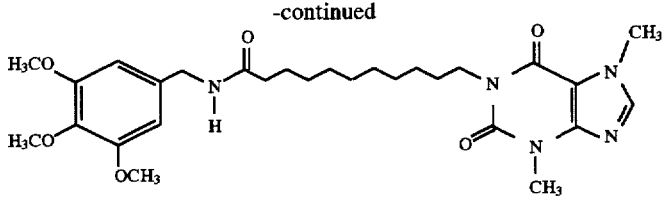

3577 1-[N(3,4,5-Trimethoxybenzyl)-11-yl-undecanamide]-3,7-dimethylxanthine

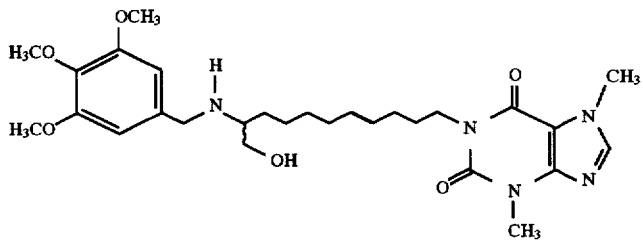

4522 1-[11-Hydroxy-10-(3,4,5-trimethoxybenzylamino)undecyl]-3,7-dimethylxanthine

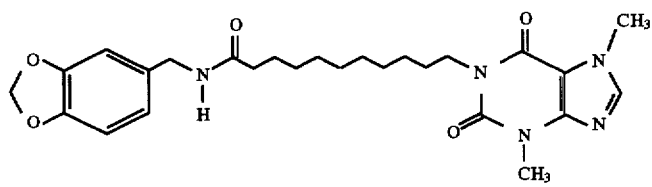

4533 1-[N-(Piperonyl)-11-yl-undecanamide]-3,7-dimethylxanthine

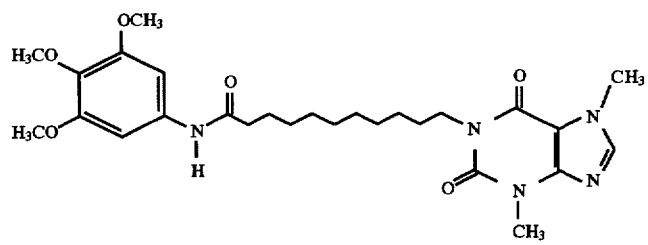

4535 1-[N-(3,4,5-Trimethoxyphenyl)-11-yl-undecanamide]-3,7-dimethylxanthine

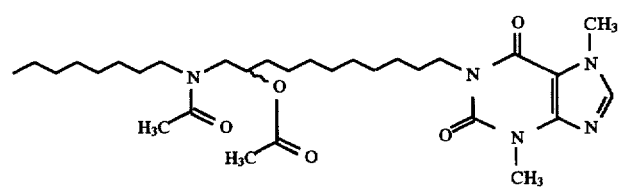

4537 1-[11-N-Octylacetamido)-10-acetoxyundecyl]-3,7-dimethylxanthine

Formulation and Dosage

Skilled artisans will recognize that form and character of a pharmaceutically acceptable carrier or diluent is dictated by, inter alia: 1) the amount of active ingredient with which it is combined; 2) the route of administration; and 3)other known variables. The route of administration of compounds useful in the inventive method is not critical but is usually oral or parenteral, preferably oral. The term parenteral, as used herein, includes intravenous, intramuscular, subcutaneous, intranasal, transdermal, opthalmic or intraperitoneal administration. Subcutaneous and intramuscular forms of parenteral administration are generally preferred.

A daily parenteral dosage regimen will preferably be from about 0.01 mg/kg to about 25 mg/kg of total body weight, most preferably from about 0.1 mg/kg to about 4 mg/kg. Preferably, each parenteral dosage unit will contain the active ingredient in an amount of from about 0.1 mg to about 400 mg.

Compounds administered according to the inventive method are generally active when given orally and can be formulated as liquids, for example, syrups, suspensions or emulsions, tablets, capsules and lozenges. A liquid formulation will generally consist of a suspension or solution of the compound or pharmaceutically acceptable salt in a suitable liquid carrier(s), for example, ethanol, glycerine, non-aqueous solvent (for example polyethylene glycol and oils) or water. A suspending agent, preservative, flavoring or coloring agent may also be added. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule.

Alternatively, a dispersion or suspension can be prepared using any suitable pharmaceutical carrier(s)—for example, aqueous gums, celluloses, silicates or oils. The dispersion or suspension can then filled into a soft gelatin capsule. The daily oral dosage regimen will preferably be from about 0.01 mg/kg to about 40 mg/kg of total body weight. Preferably, each oral dosage unit will contain the active ingredient in an amount of from about 0.1 mg to about 1000 mg.

Furthermore, skilled artisans will recognize that the optimal quantity and spacing of individual dosages of a compound or a pharmaceutically acceptable salt or hydrate or solvate thereof, useful in the inventive method, will be determined by the nature and extent of the condition being treated; the form, route and site of administration; and the particular patient being treated. Such optimums can be determined by techniques known to skilled artisans. As may be appreciated by skilled practitioners, the optimal course of treatment (i.e., the number of doses given per day and duration of therapy of a compound or a pharmaceutically acceptable salt or hydrate or solvate thereof, which are useful in the inventive method) can be ascertained by those skilled in the art using conventional treatment determination studies known in the pharmaceutical industry.

Without further elaboration, it is believed that one skilled in the art can, using the preceding description, utilize the present inventive method for treating symptoms of AD to its fullest extent. Therefore, the following examples are illustrative of specific, preferred embodiments of the invention; but these examples are not intended to be construed as limiting, in any way, the scope of the invention as disclosed herein.

EXAMPLE 1

This example is an in vitro assay confirming activity of an ability of representative agents to inhibit APP synthesis by effecting the level of alkaline phosphatase in the culture medium of human neuroblastoma cells, SH-SY5Y (Beidler et al., 1978), expression of which is controlled by a human amyloid precursor protein (APP) promoter.

The SH-SY5Y were transfected with the promoter-alkaline phosphatase reporter gene construct pHAPPro. 1, shown in FIG. 1. The transfected cells were prepared as follows:

A DNA fragment comprising nucleotide pairs −660 to +20 of the human APP promoter (Salbaum et al. 1988) was isolate by polymerase chain reaction using human placental DNA as a template. Xba I and ASP718 restriction endonuclease recognition sites were incorporated during amplification to facilitate subcloning upstream of an alkaline phosphatase reporter gene, forming the plasmid pHAPPro. 1, represented in FIG. 1. SH-SY5Y were subsequently transfected with pHAPPro. 1.

Comparing results obtained in this assay to a standard based on alkaline phosphatase expression controlled by a human phosphoglycerol kinase (PGK) promoter, relative to any cytotoxic effects an agent confirms therapeutic efficacy in the inventive method.

In all assays, controls were done in triplicate. Control assays specifically included assays using: 1) unstimulated cells; 2) cells stimulated with 1 nM hTNFα alone; 3) cells stimulated with 1 nM hTNFα and increasing concentrations of agent, as tested for all representative agents; 4) cells stimulated with 1 nM hTNFα and increasing concentrations of vehicle (100% ethanol), corresponding to vehicle concentrations in test agent preparations.

Subsequent validation of all results included repeating tests with an expanded dose range. Results obtained were compared to an agent's inhibition of constituitive promoter for the phosphoglycerol kinase gene and endogenous amyloid precursor protein expression in neuroblastoma cells Reagents are prepared as follows:

1× SEAP:

500 g Diethanolamine (liquid, Sigma CAT# D2286, St. Louis, Mo.) was brought to 600 mL with deionized $H_2O$ and the pH adjusted to 9.8 with HCl. The solution was brought to a final volume of 793 mL with deionized $H_2O$, resulting in 6M Diethanolamine (pH 9.8). The solution was stored at room temperature in a brown bottle.

11.24 g L-homoarginine was combined with 475 mL deionized $H_2O$ and dissolved by stirring. The resulting solution was brought to 500 mL total volume with deionized $H_2O$ to obtain 0.1M L-homoarginine. The solution was stored at room temperature.

28.75 g $ZnSO_4 \cdot 7H_2O$ was combined with 75 mL deionized $H_2O$ and dissolved by stirring. The resulting solution was brought to 100 mL total volume (1M $ZnSO_4$) with deionized $H_2O$ and stored at room temperature.

20.3 g $MgCl_2$ was combined with 75 mL deionized $H_2O$ and dissolved by stirring. The resulting solution was brought to 100 mL total volume with deionized $H_2O$, resulting in 1M $MgCl_2$. The solution was stored at room temperature.

3.71 g Para-nitrophenylphosphate (Sigma Chem. CO., St. Louis, Mo.) is combined with 75 ml deionized $H_2O$ and dissolved by stirring. The dissolved solution was then brought to 100 ml total volume with deionized $H_2O$, resulting in 100 mM para-nitrophenylphosphate. The solution was stored at −20° C.

Finally, all of the reagents prepared above were combined. Specifically, 166.7 ml, 6M Diethanolamine, pH 9.8; 200 ml, 0.1M L-homoarginine; 500 ml, 1M $MgCl_2$; 20 ml $ZnSO_4$; 132.8 ml deionized $H_2O$ were combined. 50 ml of this resulting solution were aliquoted to containers and stored at −20° C. to obtain 500 ml of 4× SEAP.

4 ml, 100 mM Para-nitrophenylphosphate, 100 ml 4× SEAP (both prepared above) and 256 ml of deionized $H_2O$ were combined. The dissolved solution was mixed by stirring and filtered through a 0.22 mm filter. The solution was stored at 4° C.

Samples, standards and controls were prepared as follows:

Agent:

Agent samples were supplied in 100% ethanol. Concentrations were adjusted to 5 mM, in 100% ethanol.

1 mM TNFα:

200 mg human TNFα: (Peprotech) was dissolved in PBS+1 mg/ml bovine serum albumin (fraction V). 20 ml aliquots of the solution are transferred to microcentrifuge tubes and stored at −80° C. Tubes are thawed once and then discarded.

Generally, the assay was conducted over three days using the following procedure.

DAY 1:

SH-SY5Y cells, prepared above, were plated into wells of a 96-well dish at a density of 20,000 cells per well in 100 ml AIM V medium (Gibco/BRL, Gaithersburg, Md.: CAT# 21021-019). Dishes were incubated at 5% $CO_2$ and 37° C. for 12 to 24 hours.

DAY 2:

Generally, 3 ml Polystyrene tubes were arranged in a rack as in wells of a 96-well plate. 700 ml AIM V medium containing 1 nM hTNFαwas added to each tube. Representative agents were then diluted directly into these tubes and vortexed. Culture medium was removed from the test plates and 100 ml medium (with or without agent and/or inducer) was transferred to each of three wells of the 96-well plate.

Specifically on Day 2, culture medium was changed to AIM V medium and cells were incubated for 2 hours at 5% $CO_2$ and 37° C. Test agents were diluted with 700 ml AIM V medium containing 1 nM human tumor necrosis factor α(hTNFα). Culture medium was removed and 100 ml of medium, with or without effective agent and inducer, was added to each of three wells of the 96-well plate.

DAY 3:

Culture medium (20 ml) from each well was transferred to a corresponding well of a 96-well ELISA dish and 180 ml 1× SEAP (0.5M diethanolamine (pH 9.8); 0.25 mM $MgCl_2$; 0.01 mM $ZnSO_4$; 10 mM L-homoarginine; 1 mM paranitrophenyphosphate. Berger et al., 1988.), prepared above, was added to each well. The plates were incubated 10 minutes in 5% $CO_2$ and 37° C., after which the kinetic change in absorbance at 405 nm was measured on a BIOTEK plate reader.

To measure cell viability, 8 ml Alamar Blue® (Alamar Biosciences, Sacremento, Calif.) reagent was added to each well of the original cell culture plates containing the cultured cells. The plates were incubated 3 hours in 5% $CO_2$ and 37° C. Absorbance at 570 nm and 600 nm was measured on a BIOTEK plate reader (EL312, BioTec Instruments, Inc.). Absorbance at 600 nm was subtracted from that at 570 nm and this value was recorded for analysis.

All data were imported into plotting software for analysis. Triplicate data points were averaged and standard error (from mean) was calculated using accepted standards. Average of the triplicate data points were plotted vs. agent concentration. Error bars representing a standard mean error were developed. A 50% inhibitory concentration ($IC_{50}$) in this assay is graphically evaluated. An agent concentration resulting in a 50% cell viability ($LD_{50}$) is also graphically determined.

Figure 2:
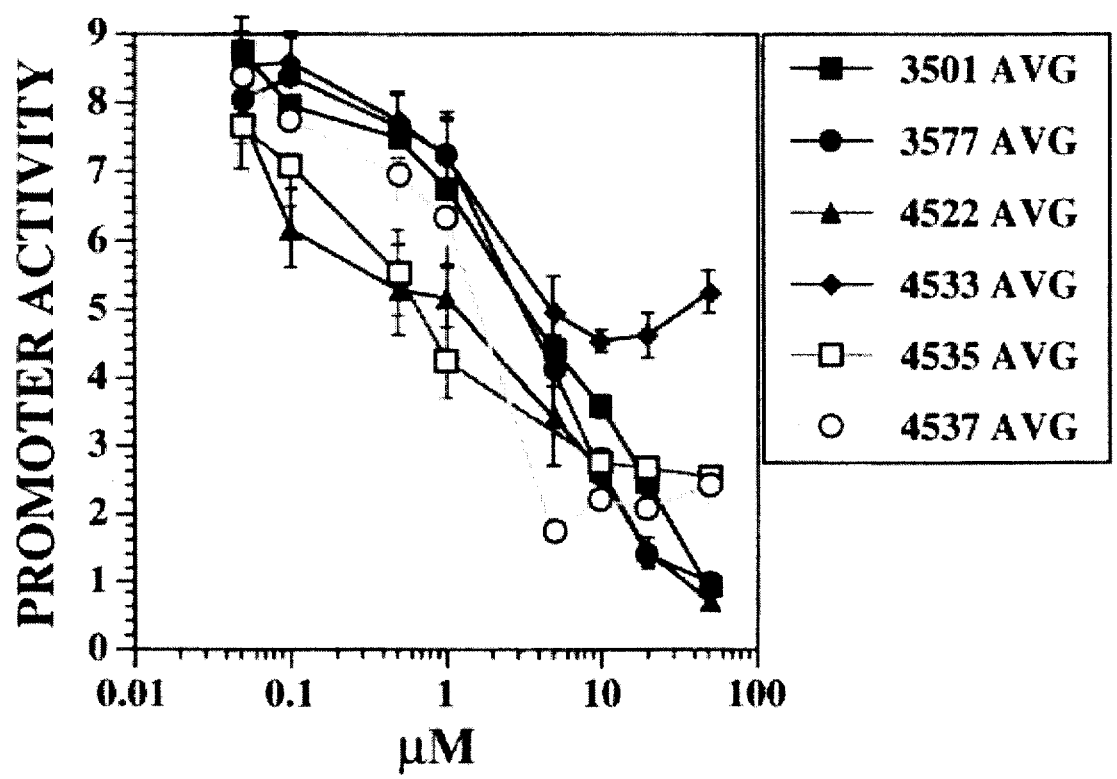
FIG. 2 illustrates an ability of compounds nos. 3501, 3577, 4522, 2533, 2535 and 4537 (see below for chemical name and structure) to inhibit APP expression in a dose-dependent fashion via the inventive method.

Data reported are shown in FIG. 2, illustrating an ability of compounds nos. 3501, 3577, 4522, 2533, 2535 and 4537 (see above for chemical name and structure) to inhibit APP expression in a dose-dependent fashion via the inventive method. As represented in FIG. 2, all compounds tested inhibited APP expression at concentrations ranging from 1–10 μM. Viability results obtained (not shown) confirm that representative compounds tested are nontoxic and have a significant therapeutic window for these representative compounds for use in the inventive method.

EXAMPLE 2

This Example illustrates the effect of representative compounds nos. 2576, 2583, 3501, 3577, 4522, 4533, 4535 and 4537 used in the inventive method on endogenous APP expression. This example shows, by Western Blot analysis, inhibition of APP expression, in a dose-dependent manner.

Cell cultures were prepared as in Example 1 using SH-SY5Y human neuroblastoma cells. Culture supernatants from SH-SY5Y cells incubated for 18 hours with 5 nM human TNFA and increasing concentrations of representative compounds identified above were separated on a 4–20% SDS-polyacrylamide gel and transferred to nitrocellulose. The nitrocellulose filter was probed with anti-APP antibody (Boehringer Mannheim, Indpls, Ind.), and the results visualized by Enhanced Chemiluminecence (Amersham Life Sciences, Arlington Heights, Ill.).

Figure 3:
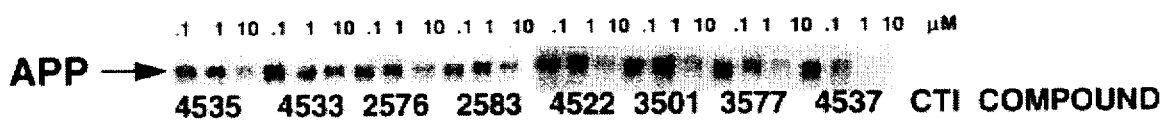
FIG. 3 illustrates that representative compounds tested inhibit expression of endogenous APP in cultured human neuroblastoma cells, correlating with data presented in FIG. 1.

FIG. 3 contains results obtained in this analysis. The data illustrate that these representative compounds tested inhibit expression of APP in cultured human neuroblastoma cells. Furthermore, inhibition of the expression of the secreted form of endogenous APP correlates with inhibition of the APP promoter in the same cells, demonstrating that these compounds are useful in the inventive method for inhibiting APP expression.

What is claimed is:

1. A method for treating symptoms of a neurodegenerative condition, comprising administering an effective amount of a compound, racemate, isolated R or S enantionmer, solvate, hydrate or salt to reduce or eliminate the symptom of the neurodegenerative condition, said compound having the formula:

X—terminal heterocyclic moiety;

wherein:

the terminal heterocyclic moiety is a 3,7-dimethylxanthinyl, 3-methylxanthinyl or xanthinyl moiety and X is:

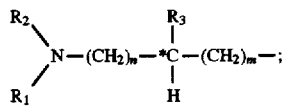

n is zero or an integer from one to four;

m is an integer from seven to fourteen:

$R_1$ and $R_2$ are hydrogen, a straight or branched chain alkyl, alkenyl or alkynyl of up to twenty carbon atoms in length or —$(CH_2)_wR_5$, w being an integer from one to twenty and $R_5$ being an hydroxyl, halo, $C_{1-8}$ alkoxyl group or a substituted or unsubstituted carbocycle or heterocycle, having one ring or two fused rings;

$R_3$ is an hydroxyl group; an oxygen atom, the single bond represented being instead a double bond; or —O—$R_4$, $R_4$ being a $C_{1-6}$ oxoalkyl.

2. The method of claim 1, wherein the compound is selected from the group consisting of:

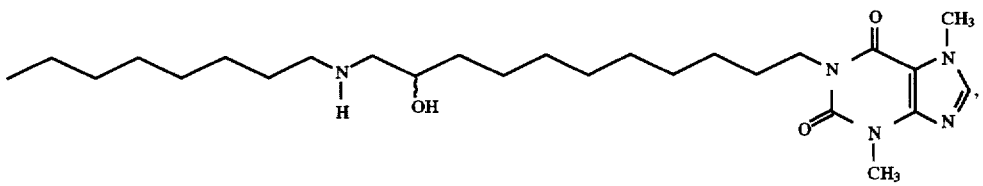

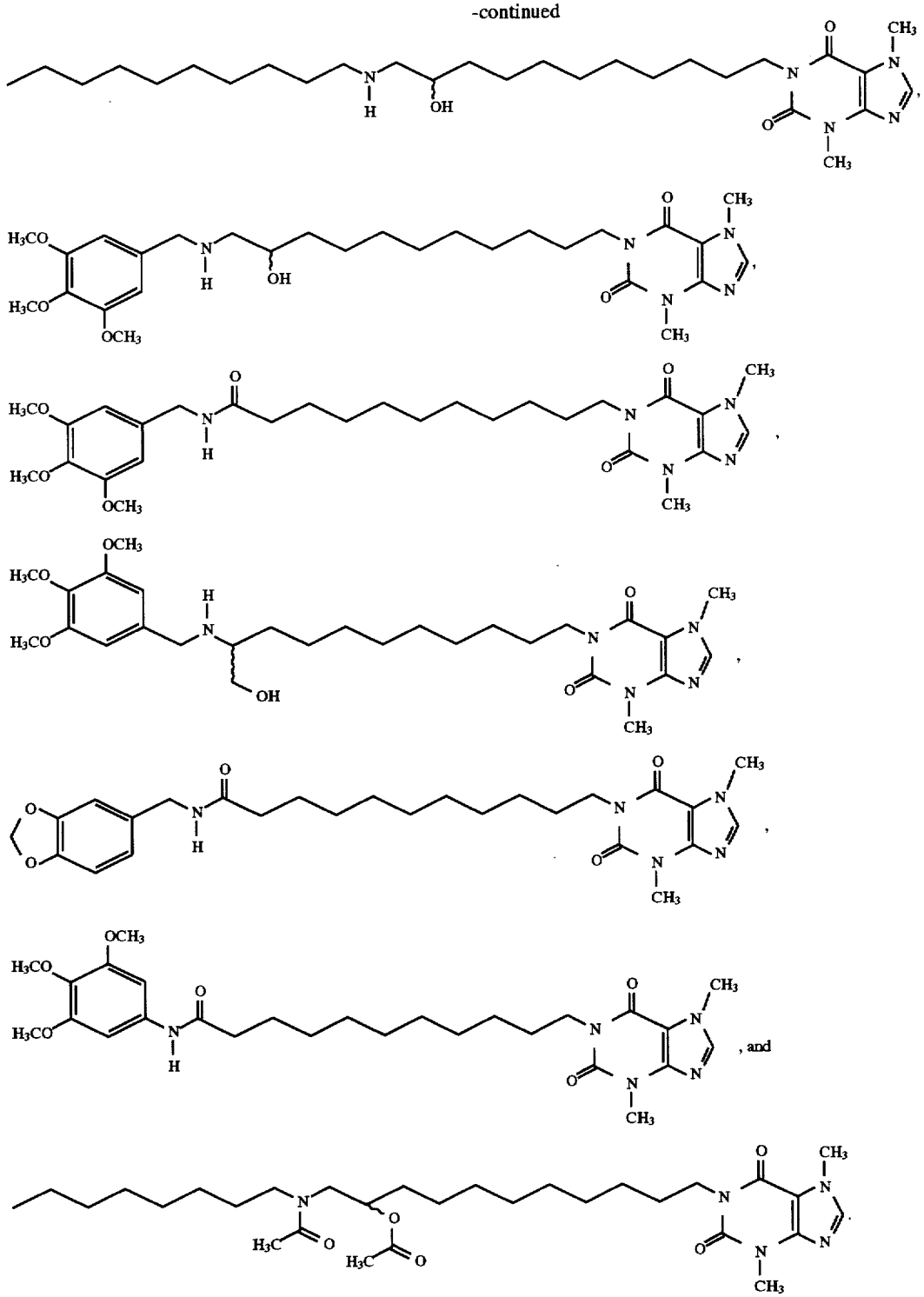

3. The method of claim 1, wherein the symptoms are selected from the group consisting of: recent memory deficit, severe memory deficit, attentive and cognitive skill deterioration, loss of language, abstract thinking, judgment and visual-spatial orientation skills, paranoia and delusion, motor deficiency, global confusion and dementia.

4. The method of claim 1, wherein treating comprises inhibiting amyloid precursor protein expression.

5. A method for inhibiting amyloid precursor protein expression comprising administering an effective amount of a compound, racemate, isolated R or S enantionmer, solvate, hydrate or salt to inhibit expression of the amyloid precursor protein having the formula:

X—terminal heterocyclic moiety;

wherein:

the terminal heterocyclic moiety is a 3,7-dimethylxanthinyl, 3-methylxanthinyl or xanthinyl moiety and X is:

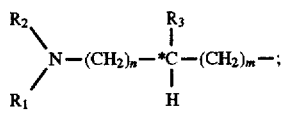

n is zero or an integer from one to four;

m is an integer from seven to fourteen;

$R_1$ and $R_2$ are hydrogen, a straight or branched chain alkyl, alkenyl or alkynyl of up to twenty carbon atoms in length or —$(CH_2)_w R_5$, w being an integer from one to twenty and $R_5$ being an hydroxyl, halo, $C_{1-8}$ alkoxyl group or a substituted or unsubstituted carbocycle or heterocycle having one ring or two fused rings;

$R_3$ may be either an hydroxyl group, an oxygen atom, the single bond represented being instead a double bond, or —O—$R_4$, $R_4$ being a $C_{1-6}$ oxoalkyl.

* * * * *